United States Patent [19]

Warnecke et al.

[11] 4,023,569

[45] May 17, 1977

[54] DEVICE FOR THE PROTECTION OF WOUNDS

[75] Inventors: Herbert Warnecke; Adolf Lindner, both of Vienna, Austria

[73] Assignee: Tuwa-Plastik Dr. Herbert Warnecke Erzeugung von Kunststoffartikeln Gesellschaft m.b.H., Vienna, Austria

[22] Filed: Sept. 18, 1975

[21] Appl. No.: 614,672

[30] Foreign Application Priority Data

Dec. 5, 1974   Austria .............................. 9762/74

[52] U.S. Cl. ............................................. 128/154
[51] Int. Cl.² ......................................... A61F 13/00
[58] Field of Search .................. 128/132, 154, 157

[56] References Cited

UNITED STATES PATENTS 3,782,377   1/1974   Rychlik .......................... 128/132 R

FOREIGN PATENTS OR APPLICATIONS

| | | | |
|---|---|---|---|
| 941,920 | 9/1948 | France ............................. | 128/154 |
| 1,291,136 | 3/1962 | France ............................. | 128/154 |
| 615,861 | 1/1949 | United Kingdom ........... | 128/132 R |
| 2,431 | 12/1895 | United Kingdom ............... | 128/154 |
| 24,352 | 12/1899 | United Kingdom ............... | 128/154 |
| 21,561 | 10/1901 | United Kingdom ............... | 128/154 |

Primary Examiner—Lawrence W. Trapp

[57] ABSTRACT

A device is provided for the protection of wounds comprising a shallow perforated bowl of substantially semi-circular cross-section terminating at its edges in substantially flat rim portions and constructed of thermoplastic material selected from the group consisting of polyethylene, polypropylene and high pressure polypropylene or such stiffness that deflection thereof by a load of 1 kg applied from the convex side to the bowl throughout its bottom surface is less than the height of the bowl measured from its bottom surface to a plane defined by the rim portions, the shape of said bowl being in the form of an elongated depression having a length more than three times its width, said bowl being gridlike and formed with apertures separated by crossing bars, the dimensions of the cross-section of the bars taken in the direction of the surface of the bowl and at right angles to that direction being from about 1:1 to 1:1.5 to each other, and the area of the apertures exceeding the grid formed by the crossing bars.

13 Claims, 7 Drawing Figures

DEVICE FOR THE PROTECTION OF WOUNDS

Wounds, such as postoperative wounds, are usually covered by a dressing. Such wounds must often be inspected by a physician. In the previous practice, the dressing covering the wound was frequently changed in the course of the healing, in most cases every day. This involved considerable staff or time and was inconvenient for the patient. In some cases the healing was adversely affected. It has also been found that a healing of wounds will be retarded if an access of air to the wounds is obstructed. Austrian Patent No. 85,023 discloses a covering for wounds which comprises a shallow bowl provided with flat rim portions. The bowl has small holes which enable a access of air to the wound. Absorptive threads are secured to the inside of the bowl and depend inwardly and are intended to absorb the matter which is secreted by the wound. These absorptive threads obstruct an access of air to the wound and, above all, such wound covering does not permit of an inspection of the wound. For this reason such wound covering must frequently be exchanged so that the wound may be adversely affected.

It is an object of the invention to provide a device for covering wounds which eliminates these disadvantages. The invention relates to such device which comprises a shallow bowl, which has apertures and which is adjoined at its edges by approximately flat rim portions. The invention essentially resides in that the device consists of elastic plastics material and the area of the apertures of the bowl exceeds the area of the solid wall portions left between the apertures. The bowl is applied so that its flat rim portions contact the skin. Because the bowl consists of elastic plastics material, these rim portions can conform to the body of the patient. The bowl itself, extends over and is spaced from the wound and owing to its large apertures permits of an inspection of the wound during the healing thereof without need for removing the device from the wound. The bowl may alternatively consist of transparent material so that the inspection is further facilitated.

According to a preferred feature of the invention the bowl is so stiff that its deflection caused by a load of 1 kg applied from the convex side to the bowl throughout its bottom surface is less than the height of the bowl measured from its bottom surface to the plane defined by the rim portions. This stiffness of the bowl ensures that the bowl does not contact the wound itself but extends over the wound and is spaced therefrom. The bowl is suitably so stiff that when its rim portions are held in position the defection caused by a load of 0.9 kg acting in a direction at right angles to the plane defined by the rim portions and applied to the convex side on a circular area 10 mm in diameter is less than the height of the bowl measured from its bottom to the plane defined by the rim portions. The elasticity of such bowl is sufficient to enable its adaptation to the shape of the body, and its stiffness is sufficient to preclude a contact of the bowl with the wound even during movements of the patient or under the load of the bedclothes or even whin the patient lies on the wound while asleep. The bowl and the rim portions may consist of synthetic thermoplastics, such as polyethylene or polyporpylene, particularly high-pressure polyethylene.

The shell is suitably gridlike and formed with apertures separated by crossing bars, and the dimensions of the cross-section of the bars in the direction of the surface of the bowl and at right angles to that direction are approximately the same or have a ratio of, at most, 1:1.5 to each other. The apertures of the bowl may be square or diamond-shaped or have the shape of rectangles or parallelograms having a side length ratio of, at most 1:1.5. According to the invention the side length of the apertures between the bars is two to four times, preferably approximately three times, the width thereof. The width of the bars may be 0.5–1.5 mm, preferably 1.2 mm. Such embodiment may desirably be produced by injection molding. According to the invention the bowl and the rim portions may alternatively consist of wire mesh, particularly of plastics material wire, the wires suitably form a braid, and the wires may be welded together at their crossings. Such bowl consisting of a wire braid may be formed together with the rim portions by hot-molding, by which the welding may be effected at the same time.

According to a preferred feature of the invention the bowl forms an elongated depression which has a length that is more than three times its width and which is preferably approximately semicircular in cross-section. This configuration enables the bowl to conform closely to postoperative wounds, which usually consist of one cut. The length of such postoperative wounds varies. According to another preferred embodiment of the invention the shallow bowl may be telescopically composed of two one-half bowl sections, which define elongated depressions. Such one-half bowl sections may be formed, e.g., in a simple manner in that one end of the elongated bowl is cut off. In this case two identical one-half bowl sections may be assembled to form wound-covering devices in various lengths and these one-half bowl sections may also be formed in larger lengths and be cut off to the desired size. The provision of two one-half bowl sections enables also an improved adaptation of the entire wound-covering device to the shape of the body part concerned. According to the invention the design may be such that the bars extend in the direction of the longitudinal axis of the depression and at right angles to said direction and the bars extending at right angles to the longitudinal axis of the depression are suitably thicker than the bars extending in the direction of the longitudinal axis of the depression. Alternatively, the bars may extend at an angle of approximately 45° to the longitudinal axis of the depression.

In accordance with the invention the inside area of the apertures may amount to 1–15 mm$^2$. It has been found that the apertures having an area of about 12 mm$^2$ enable a good inspection of the wound whereas the bowl has a sufficiently high stiffness.

Accord to a further feature of the invention the device may be silver-plated and may, in particular, have a vapor-deposited silver coating. Silver has a bactericidal acitivity so that the maintenance of the wound under sterile conditions is promoted.

In accordance with the invention the rim portions may be adhesive and for this purpose may be coated, e.g., with a pressure-sensitive adhesive. The apertures in the rim portion may be smaller in cross-section than those in the body of the bowl. If the rim portions are coated with a pressure-sensitive adhesive which is compatible with the skin, the device according to the invention may be simply adhered around the wound without need for a dressing. Alternatively, the device according to the invention may be retained on the desired part of the body of the patient by means of a dressing. In this case the access of air is restricted but is not inhibited, and only the dressing must be removed for an inspection. If the rim portions are provided with a pressure-sensitive adhesive, the device according to the invention can remain in position when the dressing is removed. In any case, a direct contact of the dressing with the wound will be avoided and the bowl need not be removed when it is desired to inspect the wound.

An embodiment of the invention is shown diagrammatically and by way of example on the drawing.

FIG. 2 is a side elevation and FIG. 1 a sectional view taken on line I—I in FIG. 2.

Figure 1:
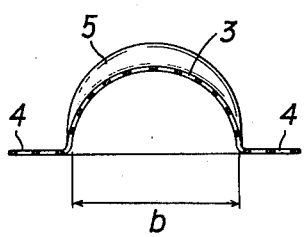
FIGS. 1 and 2 show a device having a bowl which has an elongated depression.
Figure 2:
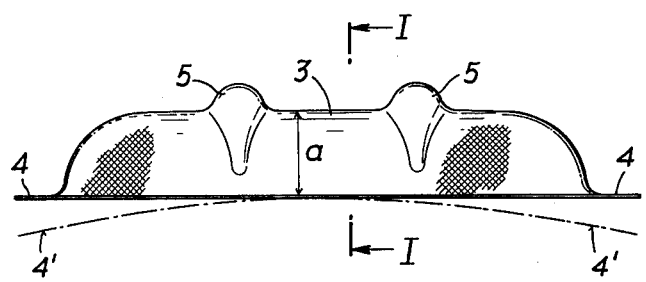
Figure 3:
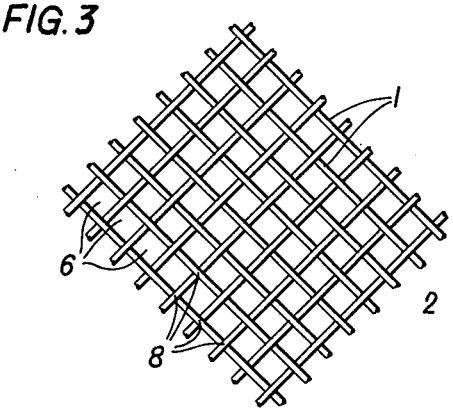
FIG. 3 is a fragmentary view showing a portion of the wire braid.

The device shown in FIGS. 1 and 2 comprises a braid of plastics material wires 1 and 2 (see FIG. 3) made of thermoplastic material. The shape of the bowl 3 and of the rim portions 4 is obtained in that a flat braid is forced into the mold under the action of heat. The depth $a$ of the depression amounts suitably to at least 12 mm and the width $b$ of the depression amounts to at most 40 mm, preferably to about 30 mm. With this width and sufficiently stiff wires it is ensured that under the loads arising in practice the bowl 3 does not deflect as far as to the plane of the rim portions 4 and for this reason does not contact the wound. Transverse bulges 5 protrude on the convex side of the bowl 3 and are reduced in height when the device is bent along its longitudinal axis in such a manner that the rim portions 4 assume the configuration indicated by the dotted line 4'. This enables a deflection of the device and an adaptation thereof to the curvature of the human body whereas the bowl does not become inwardly convex under the tensile stresses and its inside depth $a$ is not reduced. The rim portions 4 are provided on their underside with a pressure-sensitive adhesive which is compatible with the skin so that the rim portions may be stuck to the body of the patient around the wound. The wires 1 and 2 have a thickness of 0.5–1.5 mm, preferably 1.2 mm. The inside area of the apertures 6 between these wires amounts to as much as 15 mm², preferably about 12 mm². As is apparent from FIG. 3, the wires 1 and 2 are welded together at their crossings 8. The wires extend at an angle of about 45° to the longitudinal axis of the bowl 3 so that they define diamond or paralellogram-shaped apertures 6 having an axis which extends in the direction of the axis of the shallow bowl 3.

Figure 6:
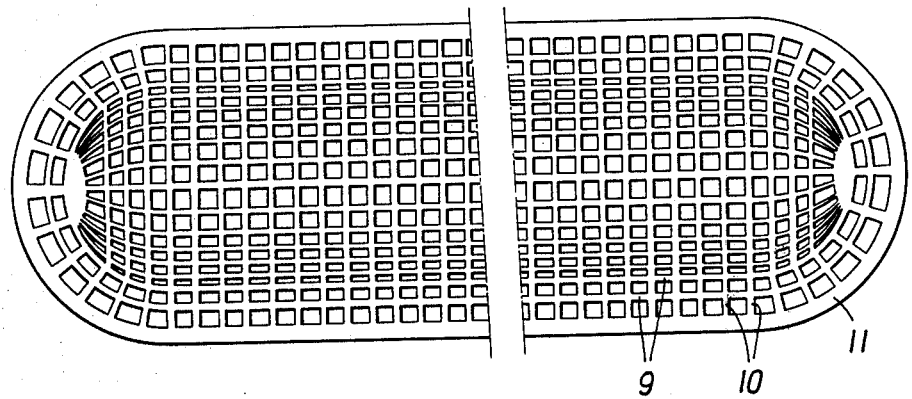
FIGS. 6 and 7 show an embodiment produced by injection molding, FIG. 6 being a top plan view and FIG. 7 a transverse sectional view.
Figure 7:
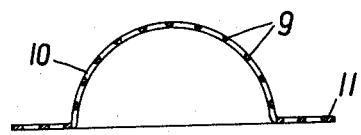

The device shown in FIGS. 6 and 7 is made by injection molding. Bars 9 extend in the longitudinal direction of the depression and the bars 10 extend transversely to the longitudinal direction of the depression. The rim portion 11 of the bowl may be coated with a pressure-sensitive adhesive and in this embodiment has no aperture at all.

Figure 4:
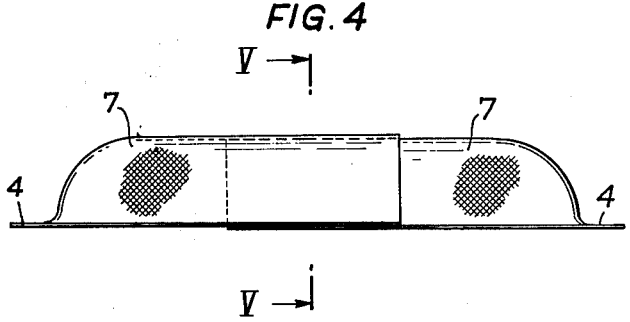
FIGS. 4 and 5 show another embodiment, FIG. 5 being a transverse sectional view taken on line V—V in FIG. 4 and FIG. 4 being a side elevation.
Figure 5:
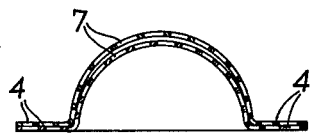

The device is primarily intended for the protection of postoperative wounds. Postoperative wounds have approximately the same width and various lengths. For this reason, an embodiment as shown in FIGS. 4 and 5 may be selected. This device is composed of two one-half bowl sections 7, which are telescopically pushed one over the other so that wounds having any desired length may be protected. In case of postoperative wounds consisting of angled or arcuate cuts, the bowls are cut at the open end at a suitable angle and are fitted together in accordance with the configuration of the cut. Owing to the elasticity of the material which is used, an overlap of up to about 10 mm may be obtained even in this case. The embodiment shown in FIGS. 4 and 5 has the same shape in cross-section as the embodiment shown in FIG. 1. This wound protection may be used in the same manner with living beings of all kinds.

We claim:

1. A device for the protection of wounds comprising a shallow perforated bowl of substantially semicircular cross-section terminating at its edges in substantially flat rim portions and constructed of thermoplastic material selected from the group consisting of polyethylene, polypropylene and high pressure polypropylene of such stiffness that deflection thereof by a load of 1 kg applied from the convex side to the bowl throughout its bottom surface is less than the height of the bowl measured from its bottom surface to a plane defined by the rim portions, the shape of said bowl being in the form of an elongated depression havng a length more than three times its width, said bowl being gridlike and formed with apertures separated by crossing bars, the dimensions of the cross-section of the bars taken in the direction of the surface of the bowl and at right angles to that direction being from about 1:1 to 1:1.5 to each other and the area of the apertures exceeding the grid formed by the crossing bars.

2. A device according to claim 1, wherein the bowl is so stiff that when its rim portions are held in position the deflection caused by a load of 0.9 kg acting in a direction at right angles to the plane defined by the rim portions and applied to the convex side on a circular area 10 mm in diameter is less than the height of the bowl measured from its bottom to the plane defined by the rim portions.

3. A device according to claim 1, wherein the apertures of the bowl are of substantially rectangular shape having a side to length ratio of, at most, 1.:1.5.

4. A device according to claim 1, wherein the bars extend in the direction of the longitudinal axis of the depression and at right angles to said direction and the bars extending at right angles to the longitudinal axis of the depression are thicker than the bars extending in the direction of the longitudinal axis of the depression.

5. A device according to claim 1 characterized in that the bars extend at an angle of about 45° to the longitudinal axis of the depression.

6. A device according to claim 1, wherein the side length of the apertures between the bars is two to four times the width of the bars.

7. A device according to claim 1, wherein the bars have a width of 0.5–1.5 mm.

8. A device according to claim 1 wherein the apertures have an inside area of 1–15 mm².

9. A device according to claim 1 wherein the bowl is silver-plated with a vapor-deposited silver coating.

10. A device according to claim 1, wherein the rim portions of the bowl are coated with a pressure-sensitive adhesive to form an adhesive rim.

11. A device according to claim 1, wherein the rim portions have apertures which are smaller than the apertures in the body of the bowl.

12. A device for the protection of wounds comprising a shallow bowl of substantially semicircular cross-section provided with apertures and terminating at its edges in substantially flat rim portions and contructed of thermoplastic material selected from the group consisting of polyethylene, polypropylene and high pressure polypropylene the shape of said bowl being in the form of two sections telescopically disposed to form an elongated depression having a length more than three times its width.

13. A device for the protection of wounds comprising a shallow bowl of substantially semicircular cross-section provided with apertures and terminating at its edges in substantially flat rim portions and constructed of thermoplastic material selected from the group consisting of polyethylene, polypropylene and high pressure polypropylene, said bowl having an elongated depression and being provided with at least one bulge which protrudes from the convex side thereof and extends transversely to the axis of the depression and up to the rim portions.

* * * * *